United States Patent
Smits et al.

(10) Patent No.: US 11,436,847 B2
(45) Date of Patent: Sep. 6, 2022

(54) OPTICAL SYSTEM AND METHOD FOR MONITORING A VEHICLE DRIVER'S EYE GAZE

(71) Applicant: Aptiv Technologies Limited, St. Michael (BB)

(72) Inventors: Soeren Smits, Neustadt (DE); Detlef Wilke, Sibbesse (DE)

(73) Assignee: Aptiv Technologies Limited, St. Michael (BB)

( * ) Notice: Subject to any disclaimer, the term of this patent is extended or adjusted under 35 U.S.C. 154(b) by 0 days.

(21) Appl. No.: 17/199,381

(22) Filed: Mar. 11, 2021

(65) Prior Publication Data

US 2021/0295071 A1    Sep. 23, 2021

(30) Foreign Application Priority Data

Mar. 19, 2020  (EP) .................................... 20164309

(51) Int. Cl.
| | |
|---|---|
| *G06V 40/19* | (2022.01) |
| *G06V 20/59* | (2022.01) |
| *H04N 5/225* | (2006.01) |
| *H04N 5/232* | (2006.01) |

(52) U.S. Cl.
CPC ............ *G06V 20/597* (2022.01); *G06V 40/19* (2022.01); *H04N 5/2252* (2013.01); *H04N 5/2256* (2013.01); *H04N 5/23245* (2013.01)

(58) Field of Classification Search
None
See application file for complete search history.

(56) References Cited

U.S. PATENT DOCUMENTS

| | | | | |
|---|---|---|---|---|
| 10,984,236 | B2 * | 4/2021 | St-Hilaire | .............. G06V 40/19 |
| 2005/0100191 | A1 * | 5/2005 | Harbach | ................ A61B 5/163 |
| | | | | 382/104 |
| 2008/0049185 | A1 | 2/2008 | Huffman et al. | |
| 2019/0188469 | A1 * | 6/2019 | Jin | ......................... G06F 1/1686 |

FOREIGN PATENT DOCUMENTS

| | | | | |
|---|---|---|---|---|
| EP | 1562102 | A2 * | 8/2005 | ............. B60K 37/06 |
| GB | 2511868 | A * | 9/2014 | ............. A61B 3/113 |
| WO | 2018164104 | | 1/2020 | |
| WO | WO-2021117031 | A1 * | 6/2021 | ......... G02B 27/0093 |

OTHER PUBLICATIONS

"Extended European Search Report", EP Application No. 20164309. 5, dated Sep. 1, 2020, 8 pages.

* cited by examiner

*Primary Examiner* — Shadan E Haghani

(74) *Attorney, Agent, or Firm* — Sawtooth Patent Group PLLC

(57) ABSTRACT

An optical system for monitoring a vehicle driver's eye gaze includes a first illumination source and a second illumination source for emitting light towards the driver's eye, a lens, and an image sensor for detecting an image, wherein the lens is configured to direct light reflected by the driver's eye to the image sensor, and wherein a distance between the second illumination source and an optical axis of the lens is larger than a distance between the first illumination source and the optical axis. Further, a method for monitoring a vehicle driver's eye gaze with an optical system is disclosed.

20 Claims, 7 Drawing Sheets

OPTICAL SYSTEM AND METHOD FOR MONITORING A VEHICLE DRIVER'S EYE GAZE

CROSS-REFERENCE TO RELATED APPLICATION

This application claims priority to European Patent Application Number 20164309.5, filed Mar. 19, 2020, the disclosure of which is hereby incorporated by reference in its entirety herein.

TECHNICAL FIELD

The present disclosure relates to an optical system and methods for monitoring a vehicle driver's eye gaze. In particular, a driver's eye gaze may be monitored by taking images of the eyes and identifying the driver's pupil in the images. Information on the driver's eye gaze may be used by a driver monitoring system or a driving assistance system, in particular of a (semi-) autonomous vehicle. The present disclosure, thus, also relates to the field of driving assistance systems.

BACKGROUND

Optical systems such as digital imaging devices, in particular digital cameras, are used in automotive applications to monitor a vehicle driver. By monitoring the driver e.g. information on the driver's attention or awareness of certain traffic situations or the driver's condition may be obtained. For example, it may be a target to recognize a condition of fatigue that can lead to a decreased capability of reacting on traffic situations.

The vehicle driver's eye gaze may be monitored in particular by identifying the driver's pupil in images taken during the drive. Based on the identified pupil, information like the direction into which the driver looks or indications of increasing fatigue may be inferred and used by a driver monitoring system or a driving assistance system to support the driver. For example, the driver may be pointed towards a potentially dangerous development in an area he is not aware of or the driver may be proposed to take a break when a condition of fatigue is noticed.

Using an optical system, the driver's face may be illuminated by an illumination source and reflected light may be focused to an image sensor by a lens. To enable discrimination of the driver's pupil in the image, the optical system may be configured as a bright-pupil system with the illumination source being arranged close to the lens, such that the emitted light reaches the driver's eye under a small angle with the optical axis of the lens. In such an arrangement, a huge amount of light reflected by the retina is directed towards the lens and the pupil may be distinguished from the iris as a bright spot, similar to the red-eye effect occurring when taking pictures with a flash. Alternatively, the illumination source may be arranged comparably far away from the lens in a dark-pupil system, such that light reflected from the retina does not reach the lens and the pupil appears as a dark spot.

The discriminability of the driver's pupil, however, also depends on external factors like the driver's size, individual eye differences or the ambient light. To account for this, a huge safety margin is required in dark- or bright-pupil systems to prevent the pupil being captured as an indistinguishable greyish spot. However, in particular in small packaged cameras required in automotive applications, design options are strongly restricted by the limited construction space and the achievable minimum distance between an illumination source and a lens, aggravating reliable pupil discrimination. In the worst case, unprevented accidents that could be preventable if driver's eye gaze data were properly provided may result.

Accordingly, there is a need for an improved optical system and methods to reliably monitor a vehicle driver's eye gaze.

SUMMARY

The present disclosure provides an optical system, a computer implemented method, a computer system and a non-transitory computer readable medium according to the independent claims. Embodiments are given in the subclaims, the description and the drawings.

In one aspect, the present disclosure is directed at an optical system for monitoring a vehicle driver's eye gaze at least including a first illumination source and a second illumination source for emitting light towards the driver's eye, a lens, and an image sensor for detecting an image, wherein the lens is configured to direct light reflected by the driver's eye to the image sensor, and wherein a distance between the second illumination source and an optical axis of the lens larger than a distance between the first illumination source and the optical axis.

The optical system, thus, is designed asymmetrically in the sense that the first illumination source and the second illumination source are located at different distances from the optical axis or the center of the lens. The first illumination source may be configured as an on-axis illumination source emitting light towards the driver's eye under a small angle with the optical axis of the lens, while the second illumination source may be configured as an off-axis illumination source emitting light towards the driver's eye under a comparably large angle with the optical axis. The optical system accordingly can be operated as a bright-pupil system by activating the first illumination but also as a dark-pupil system by activating the second illumination source, thus enabling to flexibly switch between a bright-pupil mode and a dark-pupil mode to account for varying environmental conditions and reliably provide eye gaze data for drivers with different physiologies.

To monitor the driver's eye gaze, images of the driver's eye may be taken in consecutive time frames of a predefined duration by the optical system, in which the pupil may be identified by an image evaluation system or algorithm. The duration of the time frames may be very short, e.g. 16.67 ms (sixteen point six seven milliseconds), such that the optical system may be understood as essentially filming the driver, in particular the driver's face and the driver's eyes, to monitor the driver's eye gaze.

For example, the system may be operated as a bright-pupil system if a distance between the driver's eyes and the optical system is comparably large, such that a sufficiently small angle between a connection line from the first illumination source to the driver's eye and the optical axis to distinguish the pupil as a bright spot results. The distance between the driver's eyes and the optical system, may, e.g., depend on the driver's size and preferred driving position or a seat adjustment. Further, the bright-pupil mode may be favored in conditions of dark ambient light. On the other hand, if the distance between the driver's eyes and the optical system is found to be small, large angles between a connection line from the second illumination source to the driver's eye and the optical axis result and the optical system may favorably be operated as a dark-pupil system by solely activating the second illumination source. Further, the optical system may be operated as a mixed system by simultaneously activating both illumination sources.

Hence, due to the asymmetric arrangement of the illumination sources, the optical system is not restricted to a pure dark-pupil system or a pure bright-pupil system but offers to flexibly switch the operation mode to a preferred operation mode in dependence on the actual conditions. The mixed operation mode may add further flexibility to the system and may be used to combine the information from the dark-pupil mode and the bright-pupil mode in case neither the bright-pupil mode nor the dark-pupil mode alone provide reliable data. In these cases, the mixed operation mode may allow to still obtain an image in which the pupil may be distinguished. Further, it has been found that for most situations, reliable pupil discrimination may be achieved by operating the optical system in either the dark-pupil mode or the mixed operation mode. Hence, it may be chosen to operate the optical system in dependence on the actual situation in one of these two operation modes.

Further, with the asymmetric design of the optical system, the safety margin for the bright-pupil mode and the dark-pupil mode may be drastically reduced. In case the pupil appears as an indistinguishable grey spot in an image taken in the bright-pupil mode or the mixed operation mode, the angle between light emitted from the first illumination source to the driver's eye and the optical axis of the lens is on the border between providing a bright spot depiction of the pupil and a dark spot depiction of the pupil. Hence, the angle between light emitted from the second illumination source to the driver's eye and the optical axis of the lens, which is by construction larger than the angle of light emitted from the first illumination source, will be well above the border for providing a dark spot depiction of the pupil. By operating the optical system in the dark-pupil mode, clear pupil discrimination may be achieved in this case. Vice versa, if the angle between light emitted from the second illumination source to the driver's eye and the optical axis of the lens is on the border between yielding a bright and a dark spot depiction of the pupil, the bright-pupil and/or the mixed pupil mode provide a clear depiction of the pupil.

Thus, occurrences of greyish pupil depictions in the bright-pupil mode and the dark-pupil mode may be acceptable since the optical system always offers another operation mode in which clear pupil discrimination may be provided. With this reduction of the necessary safety margin, the optical system may in particular be suited and configured as a small package camera system for automotive applications. In particular since the distance between the lens and the second illumination source does not have to be large enough to guarantee the discriminability of the pupil as a dark spot in every image or situation, the optical system may be designed sufficiently small while ensuring a reliable driver's eye gaze monitoring.

In addition to the mixed operation mode, the pure dark-pupil mode, and the pure bright-pupil mode, the optical system may provide a reflection reduction mode in which the first illumination source and the second illumination source are activated alternately in consecutive time frames. This reflection reduction mode enables to actively reduce the impact of light that is reflected before reaching the driver's eye and thus aggravates the identification of the pupil in the image, in particular in case the driver is wearing glasses. By alternately taking images with the first illumination source activated and the second illumination source activated, reflections on glasses may be reduced and the optical system may provide images with a distinguishable depiction of the pupil even under such complex circumstances.

Hence, the optical system may in principle be operated in a mixed operation mode in which both illumination sources are activated simultaneously in a time frame in which an image of the driver's eye is taken. Further, the optical system may be operated in a pure operation mode, in which either the first illumination source or the second illumination source is activated in a time frame, while the respective other illumination source is deactivated. The pure operation mode may in particular include a bright-pupil mode in which the first illumination source is activated and a dark-pupil mode in which the second illumination source is activated. Additionally, the pure operation mode may include a refection reduction mode in which the first illumination source and the second illumination source are activated alternately in consecutive time frames. In a sense, the reflection reduction mode may be understood as a combination of the dark-pupil mode and the bright-pupil mode in which said modes are used alternately in consecutive time frames.

The optical system may include a controller configured to determine a preferred operation mode of the mixed operation mode and the pure operation mode for an upcoming time frame and operate the optical system in the preferred operation mode in the upcoming time frame. In particular, the preferred operation mode may be one of the mixed operation mode, the bright-pupil mode, the dark-pupil mode and the refection reduction mode, while it is also possible that the bright-pupil mode is only realized as a part of the refection reduction mode. The controller may be configured to carry out a method for monitoring a driver's eye gaze described herein. In particular, the controller may include a CPU, a microprocessor or a similar processing unit.

In another aspect, the illumination sources may emit light in the infrared region. In particular, the illumination sources may be vertical-cavity surface-emitting lasers (VCSEL), light-emitting diodes (LED) or other infrared light emitting sources.

In another aspect, the first illumination source, the second illumination source, the lens and the image sensor are arranged in a common housing. Hence, the optical system may form a compact object and in particular be configured as a small packaged driver monitoring camera for automotive applications. By arranging the components of the optical system in a common housing, the optical system may be easily mounted in a vehicle without the illumination sources having to be mounted at different locations of the vehicle.

The lens may be arranged between the first illumination source and the second illumination source. Further, the first illumination source, the lens and the second illumination source may be arranged in alignment. In particular, the first illumination source, the second illumination source and the lens may be aligned along a line that is perpendicular to the optical axis of the lens, providing a clear geometry.

According to another aspect, a distance between the second light source and the center of the lens is larger than three times a distance between the first light source and the center of the lens, in particular wherein the distance between the first light source and the center of the lens is smaller than or equal to 12 mm and the distance between the second light source and the center of the lens is larger than or equal to 40 mm.

By keeping the distance between the second illumination source and a center of the lens at least three times the distance between the first illumination source and the center of the lens, the difference between an angle between light emitted from the second illumination source towards the driver's eye and the optical axis of the lens and an angle between light emitted from the first illumination source towards the driver's eye and the optical axis can also be ensured to be comparably large. This may ensure reliable pupil discrimination in at least one of the provided operation modes.

Further, it has been found that by arranging the second illumination source at a minimum distance of 40 mm to the center of the lens, it may be ensured that an angle between light emitted from the second illumination source to the driver's eye and the optical axis is large enough to enable pupil discrimination in the dark-pupil mode for a significant range of typical distances between the driver's eye and the optical system. With increasing distance between the second illumination source and the lens, a sufficiently large angle may also be realized at larger distances between the driver's eye and the optical system, increasing the range of typical eye distances for which the dark-pupil mode works reliable.

Similarly, a maximum distance of 12 mm between the first illumination source and the center of the lens has been found to reliably enable pupil discrimination in particular for comparably large distances between the driver's eye and the optical system in the bright-pupil mode in which only the first illumination source is activated or in the mixed operation mode.

Further, it has been found that by constructing the optical system with a minimum distance between the second illumination source and the center of the lens of 40 mm and a maximum distance between the first illumination source and the center of the lens of 12 mm, reliable pupil discrimination may be achieved by using either the mixed operation mode or the dark-pupil mode.

In another aspect, a distance between the first illumination source and the second illumination source is at least 50 mm. This has been found to be the minimum distance between the illumination sources enabling active reflection reduction in a reflection reduction mode in which the illumination sources are alternately activated in consecutive time frames. Hence, the optical system may be configured as a small packaged driver monitoring system reliably providing pupil discrimination with an extension of only slightly more than 50 mm in a direction in which the components of the optical system are aligned.

According to another aspect, the first illumination source, the second illumination source and the lens are arranged such that for a range of expected driver's eye distances, a driver's eye distance being a distance between the driver's eye and the center of the lens along the optical axis of the lens, at least one of the following conditions is fulfilled: a first angle between a connection line from the first illumination source to the expected location of the driver's eye and the optical axis is equal to or smaller than a predefined bright-pupil angle, in particular wherein the bright-pupil angle equals 1°, and/or a second angle between a connection line from the second illumination source to the expected location of the driver's eye and the optical axis is larger than a predefined dark-pupil angle, in particular wherein the dark-pupil angle equals 5°, and/or a difference angle between the second angle and the first angle is larger than a predefined grey-pupil-shifting angle.

For example, a typical range of driver's eye distances may be 400 mm to 900 mm, with the actual driver's eye distance e.g. depending on the driver's size. If the first condition is fulfilled and the first angle is smaller than the bright-pupil angle, the driver's pupil may reliably be identified in the bright-pupil mode in which only the first illumination source is activated. In particular, it has been found that for a first angle smaller than 1°, the bright-pupil mode works reliably. Hence, the bright-pupil mode may be the preferred operation mode for large driver's eye distances.

In case the second condition is fulfilled, the driver's pupil may reliably be identified in the dark-pupil mode in which only the second illumination source is activated. This operation mode may especially be the preferred operation mode for small driver's eye distances.

In a range for which neither the first nor the second condition may be fulfilled, grey pupil occurrence is likely in at least one of the bright-pupil mode or the dark-pupil mode. If a grey and undistinguishable pupil is detected e.g. in the bright-pupil mode, then the first angle is on the border between allowing the pupil to be identified as a bright spot and allowing the pupil to be identified as a dark spot. However, since the second angle is the sum of the first angle and the difference angle, the second angle will always be large enough to obtain a clearly distinguishable depiction of the pupil as a dark spot as long as the difference angle is large enough, in particular larger than a predefined grey-pupil shifting angle. Hence, by switching to the dark-pupil mode in such a situation, a clearly distinguishable pupil may be obtained.

Vice versa, if the optical system is operated in the dark-pupil mode and a grey pupil occurs, the second angle is on the border between obtaining a dark pupil and obtaining a bright pupil. In this case, the first angle being the difference between the second angle and the difference angle will always be small enough to reliably provide a depiction of the pupil as a distinguishable bright spot if the difference angle is large enough. Thus, if the third condition is fulfilled and a grey pupil occurs, switching the operation mode always and reliably leads to a defined pupil response. Further, it has been found that for most of the expected range of driver's eye distances, the dark-pupil mode and the mixed operation mode are sufficient, such that switching between those operation modes may be realized. In addition, the bright-pupil mode may still be available as a part of a reflection reduction mode with alternately activated illumination sources, which may be the preferred mode if the driver is wearing glasses.

The grey-pupil-shifting angle may depend on the distinct properties of the optical system, e.g. the illumination sources that are used. In general, a minimum value of the grey-pupil-shifting angle of 1°, 1.5°, 2°, 2.5° or 3° may be sufficient.

In another aspect, the present disclosure is directed at a computer implemented method for monitoring a vehicle driver's eye gaze with an optical system, in particular an optical system according to one of the aspects disclosed herein, the optical system including at least a first illumination source and a second illumination source for emitting light towards the driver's eye and a lens for directing light reflected by the driver's eye to an image sensor, wherein a distance between the second light source and an optical axis of the lens is larger than a distance between the first light source and the optical axis, and wherein in consecutive time frames at least one image of the driver's eye is detected per time frame, wherein the method includes at least the following steps: determining a preferred operation mode of the optical system for an upcoming time frame, the preferred operation mode being one of at least a mixed operation mode and a pure operation mode, and operating the optical system according to the preferred operation mode in the upcoming time frame.

For example, the method may be carried out by a computer hardware component like a CPU or a microprocessor.

The pure operation mode may include a dark-pupil mode with the second illumination source being activated, a bright-pupil mode with the first illumination source being activated, and/or a reflection reduction mode with the first illumination source and the second illumination source being activated alternately in subsequent time frames.

As has been mentioned, the asymmetric arrangement of the illumination sources offers a variety of different operation modes, each of which may allow obtaining an image with clear pupil discrimination under certain conditions. By determining a preferred operation mode of these operation modes, in particular given an actual situation, and operating the optical system in the preferred operation mode, the optical system may flexibly be adjusted to ensure that an image with proper pupil discriminability is taken, even under varying environmental conditions. For example, the optical system may be switched from, e.g., a dark-pupil system to a bright-pupil system if the driver passes a tunnel and the ambient light suddenly decreases, such that the bright-pupil mode is the preferred operation mode. Further, in case it is recognized that the driver is wearing glasses, the reflection reduction mode may be determined as the preferred operation mode and the optical system may be switched to the reflection reduction mode, if the optical system has not been operated in the reflection reduction mode already.

The preferred operation mode may be determined at the beginning of the upcoming time frame. Alternatively, the preferred operation mode may be determined at the end of a preceding time frame, such that the upcoming time frame following the preceding time frame may be started with the preferred operation mode already determined. In general, the preferred operation mode may be determined in a first step and the optical system may be operated in the preferred operation mode in a subsequent step. Further, the preferred operation mode may be determined for each upcoming time frame, i.e. separately for consecutive time frames, or the preferred operation mode may be repeatedly determined after a preset number of time frames for an upcoming time frame, or the preferred operation mode may be determined at the start of the system.

According to another aspect, the preferred operation mode is determined based on at least one gauge parameter, the gauge parameter being at least one of: a distance parameter representing an estimated and/or a measured distance between the driver's eye and the optical system, in particular a distance between the driver's eye and a center of the lens along the optical axis; a brightness parameter representing a brightness of ambient light; a reflection parameter representing a gauge and/or a measure of an amount of light being reflected before reaching the driver's eye; a pupil size estimation parameter representing an estimated and/or measured size of the driver's pupil; and a discriminability parameter representing the discriminability of the driver's pupil in at least one image detected with the image sensor during at least one preceding time frame operated in a current operation mode, the current operation mode being one of the mixed operation mode and the pure operation mode.

In general, the gauge parameter may be any parameter or include any combination of parameters that affect the pupil discriminability in the different operation modes of the optical system. For example, values of the gauge parameter may be assigned a preferred operation mode. Thus, the value of the gauge parameter may be determined and the preferred operation mode may be determined by reading out a look-up table storing such an assignment. Subsequently, the optical system may be operated in the determined preferred operation mode.

For example, the gauge parameter may be or include a distance parameter representing an estimated and/or a measured distance between the driver's eye and the optical system, in particular a distance between the driver's eye and a center of the lens along the optical axis. For example, the optical system may include an optical sensor to measure this distance.

For very small distances between the driver's eye and the optical system, it may not be possible to achieve a sufficiently small angle between light emitted from the first illumination source towards the driver's eye and the optical axis to detect the pupil as a bright spot in an image. However, for such a distance, comparably large angles between light emitted from the second illumination source and the optical axis result, such that a dark-pupil mode in which only the second illumination source is activated may be determined as the preferred operation mode. Vice versa, for very large distances between the driver's eye and the optical system, a bright-pupil mode in which only the first illumination source is activated may be determined as the preferred operation mode. For medium distances, e.g. the mixed operation mode with both illumination sources being activated simultaneously may be determined as the preferred operation mode.

The gauge parameter may also be or include a brightness parameter representing a brightness of ambient light. For instance, if dark ambient light conditions are ascertained, the bright-pupil mode may be determined as the preferred operation mode. The brightness parameter may in particular represent an absolute measure of the brightness of ambient light. The brightness parameter may also indicate a change of the brightness of ambient light.

Further, the gauge parameter may be or include a reflection parameter representing an estimate and/or a measure of an amount of light being reflected before reaching the driver's eye. In particular, when the driver is wearing glasses, light emitted from the illumination sources may be reflected from the glasses and distort the image and the discriminability of the driver's pupil. To actively reduce such reflections, the pure operation mode may include a reflection reduction mode in which the first illumination source and the second illumination source are activated alternately in subsequent time frames. Hence, in case a driver wearing glasses is detected, e.g. by an image evaluation system or algorithm in an image taken in a preceding time frame, the reflection reduction mode may be determined as the preferred operation mode. Accordingly, a value of the reflection parameter may indicate whether or not the reflection reduction mode is recommended and the reflection parameter may be calculated by a reflection recommendation algorithm based on at least one image taken in preceding time frames. In particular, the reflection parameter may be a Boolean parameter representing a binary decision whether or not the reflection reduction mode should be used.

Further, the gauge parameter may be or include a pupil size estimation parameter representing an estimated and/or measured size of the driver's pupil. For instance, the driver's pupil size may be determined in images taken in preceding time frames by an image evaluation system or algorithm. The driver's pupil size may, for example, change in dependence on the brightness of ambient light and also influence the discriminability of the pupil in images taken in the different operation modes, such that for a respective pupil size, a preferred operation mode may be assigned.

Alternatively or additionally, the gauge parameter may be or include a discriminability parameter representing a discriminability of the driver's pupil in at least one image detected with the image sensor during at least one preceding time frame operated in a current operation mode, the current operation mode being one of the mixed operation mode and the pure operation mode. For example, the optical system may have been operated in a current operation mode for a certain number of consecutive time frames and the discriminability parameter may be a counter of images with improper pupil identification in these time frames. A threshold value may be preset defining a maximum number of images with improper pupil discrimination acceptable and in case the value of the discriminability parameter exceeds the threshold value, another operation mode than the current operation mode may be determined as the preferred operation mode while the current operation mode may be determined as the preferred operation mode as long as the discriminability parameter does not exceed the threshold. In particular, the current operation mode may be one of the mixed operation mode and the pure operation mode and the other of the mixed operation mode and the pure operation mode may be determined as the preferred operation mode if the discriminability parameter exceeds the threshold value. Alternatively, switching between a bright-pupil mode and a dark-pupil mode based on the discriminability parameter may also be realized.

Hence, a CPU, a microprocessor or another processing device may be configured to determine the preferred operation mode based on the gauge parameter. A value of the gauge parameter may be determined and sent to the CPU or a processing device to enable considering the gauge parameter in determining the preferred operation mode.

According to another aspect, the preferred operation mode is one of a current operation mode of the mixed operation mode and the pure operation mode and the other of the mixed operation mode and the pure operation mode, wherein determining the preferred operation mode includes: determining, based on the gauge parameter, whether it is necessary to switch from the current operation mode to the other operation mode in order to obtain an image in which the driver's pupil is distinguishable in the upcoming time frame; and determining the other operation mode as the preferred operation mode if the gauge parameter indicates a necessity to switch to the other operation mode.

The optical system may in general be operated in a current operation mode in a time frame preceding the upcoming time frame. Determining the preferred operation mode for the upcoming time frame may be conducted by checking whether a switch to the respective other operation mode is necessary in order to obtain an image with proper pupil discrimination. For example, based on a brightness parameter indicating a sudden change of the brightness of ambient light or on a discriminability parameter showing that the pupil could not be identified in at least one preceding time frame, a necessity to switch to the other operation mode may be indicated and the other operation mode may, accordingly, be determined as the preferred operation mode. In particular, the current operation mode may be one of the mixed operation mode and a dark-pupil mode that may be included by the pure operation mode.

The gauge parameter, according to another aspect, includes at least the discriminability parameter, wherein a value of the discriminability parameter is a counter of images with improper pupil discrimination detected in preceding time frames consecutively operated in the current operation mode, wherein the other operation mode is determined as the preferred operation mode if the discriminability parameter exceeds a preset discrimination threshold value defining a maximum number of images with improper pupil discrimination.

Vice versa, in case the discriminability parameter does not exceed the preset discrimination threshold value, the current operation mode may be determined as the preferred operation mode. By tracking images with improper pupil discrimination, it may be checked whether the current operation mode reliably provides images in which the driver's pupil is distinguishable or not. In case any external conditions affecting the pupil discriminability in the current operation mode change, the discriminability parameter may ensure to switch to the preferred operation mode for these specific circumstances with only a small and acceptable number, the threshold value, of images with improper pupil discrimination being taken.

It will be understood that, while it is described to determine the other operation mode as the preferred operation mode whenever the discriminability parameter exceeds the present threshold value, it may be chosen to switch the operation mode in case the discriminability parameter equals the preset threshold value. In case the method e.g. involves an instruction in a software program to switch the operation mode when the discriminability parameter equals a certain value, the threshold value may be understood as the nearest possible value of the discriminability parameter to said certain value used in the instruction.

According to another aspect, the value of the discriminability parameter is incremented by one count if an image with improper pupil discrimination is detected in a time frame and if at least one gaze parameter is detected to be in a predefined appropriate range, the at least one gaze parameter being at least one of a driver's head yaw, a driver's eye lid opening and/or a distance between a driver's head or face and the optical system.

By assuring that the at least one gaze parameter is in an appropriate range, false identification of an image as an image with improper pupil discrimination may be prevented. For example, an image may be taken in a time frame during which the driver turned his head such that the driver's eye is not on the image taken in this time frame. Hence, by checking the driver's head yaw, it can be prevented that such an image is considered as an indication that the current operation mode is not appropriate and potentially should be switched. On the other hand, if it is detected that the driver's pupil could not be discriminated in an image while the driver was straightly looking towards the optical system, this image may be counted as an image with improper pupil discrimination and an indication that the current operation mode of the optical system is not suited for the actual situation.

In particular, a CPU or a microprocessor may be configured to perform the steps for calculating a value of the discriminability parameter. The gaze parameter may, e.g., be determined by an image evaluation algorithm carried out by the CPU or the microprocessor.

In particular, according to another aspect, the value of the discriminability parameter is incremented by one count if an image with improper pupil discrimination is detected in a time frame and if at least the driver's head yaw and the driver's eye lid opening are in a predefined appropriate range. Hence, it may be ensured that an image is only considered as an indication that the operation mode should be switched if the driver's pupil could not be identified while the driver was looking straightly towards the optical system with open eyes.

Further, according to another aspect, the value of the discriminability parameter is decremented by one count if an image with proper pupil discrimination is detected in a time frame. Hence, randomly occurring images with improper pupil discrimination in the current operation mode, for example due to shadows changing the ambient light for a very short period of time, may be compensated and unnecessary switches to the other operation mode may be prevented.

According to another aspect, the pure operation mode includes a dark-pupil mode in which the second illumination source is at least temporarily activated in the upcoming time frame and the first illumination source is deactivated in the upcoming time frame, wherein the dark-pupil mode is determined as the preferred operation mode if the mixed operation mode is the current operation mode and if the value of the discriminability parameter exceeds the threshold value.

It has been found that, while a bright-pupil mode may be useful and add further flexibility to the optical system, reliable pupil discrimination may already be achieved by providing a pure dark-pupil mode and the mixed operation mode in which both illumination sources are activated simultaneously for at least most situations. Hence, the optical system may be switched between the mixed operation mode and the dark-pupil mode in case the value of the discriminability exceeds the threshold value in the current operation mode, which accordingly may be one of the mixed operation mode and the dark-pupil mode. This enables to easily and quickly determine the preferred operation mode as one of two operation modes without a necessity of complicated and sophisticated algorithms requiring high computational resources.

According to another aspect, the pure operation mode includes a reflection reduction mode in which one of the first illumination source and the second illumination source is at least temporarily activated while the other one of the first illumination source and the second illumination source is deactivated in the upcoming time frame and in which the other one of the first illumination source and the second illumination source is at least temporarily activated while the one of the first illumination source and the second illumination source is deactivated in a subsequent time frame following the upcoming time frame.

Thus, the first illumination source and the second illumination source are activated alternately in subsequent time frames in the reflection reduction mode. This enables to actively reduce reflections of light before the light reaches the drivers eye, for example when a driver is wearing glasses. In principle, the reflection reduction mode may also be realized in shortened time frames, e.g. such that the duration of a time frame in the reflection reduction mode may be half of a duration of a time frame in the mixed operation mode or in a dark-pupil mode or a bright-pupil mode.

The preferred operation mode is, according to another aspect, determined based on at least a reflection parameter representing an estimate and/or a measure of an amount of light being reflected before reaching the driver's eye, wherein the reflection reduction mode is determined as the preferred operation if the reflection parameter indicates a high amount of light emitted towards the driver's eye being reflected before reaching the driver's eye. In particular, the reflection parameter may be included by the aforementioned gauge parameter. In particular, the value of the reflection parameter may indicate a recommendation for using the reflection reduction mode and whenever the reflection reduction mode is recommended, it may be determined as the preferred operation mode. Thus, the reflection parameter may be a Boolean parameter representing a binary decision whether the reflection reduction mode is recommended or not. Alternatively, a value of the reflection parameter may represent an impact of reflections on images taken in preceding time frames and the reflection reduction mode may be determined as the preferred operation mode if the impact value exceeds a certain threshold value.

The reflection parameter may, e.g., be determined by a reflection estimation software program carried out by a CPU or a microprocessor. For example, the reflection estimation software program may be performed to detect whether the driver is wearing glasses in an image taken with the image sensor and accordingly assign a value to the reflection parameter. The CPU or the microprocessor may be configured to determine the preferred operation mode based on the reflection parameter.

The gauge parameter may, according to another aspect, include at least a reflection reduction parameter and a discriminability parameter. In such a case, a decision based on the reflection parameter may be superior to a decision based on the discriminability parameter. Hence, it may be determined in a first step whether the reflection reduction mode is the preferred operation mode based on the reflection parameter. Subsequently and only in case the reflection reduction mode is not recommended, i.e. not the preferred operation mode, another operation mode may be determined as the preferred operation mode and decisions based on the discriminability parameter may follow. The preferred operation mode may be determined accordingly for each upcoming time frame. In particular, these steps to determine the preferred operation mode may be performed by a computer hardware component like a CPU or a microprocessor.

According to another aspect, the first illumination source and/or the second illumination source are activated for a respective activation time in the mixed operation mode and in the pure operation mode, wherein a maximum activation time in the mixed operation mode is half of an exposure time of the optical system in the time frames, in particular wherein the maximum activation time in the mixed operation mode is half of a maximum activation time in the pure operation mode and a minimum activation time in the mixed operation mode is half of a minimum activation time in the pure operation mode. The maximum activation time in the pure operation mode may, thus, in particular equal the exposure time of the optical system.

Since in the mixed operation mode both illumination sources are activated simultaneously while in the pure operation mode, only one of the illumination sources is activated, a similar activation time in both operation modes would result in different signal to noise ratios, thus aggravating image evaluation. However, by normalizing the activation time to the number of active illumination sources, a similar signal to noise ratio may be obtained in both operation modes.

The maximum activation time, the exposure time and/or the minimum activation time may be image sensor specific and may depend on the image sensor performance, in particular the efficiency of the image sensor in the infrared region. However, the maximum activation time may be 2 ms (two milliseconds) in the pure operation mode or smaller.

A CPU, a microprocessor or a similar computer hardware component may be configured to activate the illumination sources.

According to another aspect, the activation time is updated after a specified number of time frames according to a medium brightness value of images detected in the specified number of time frames, in particular wherein the medium brightness value represents a medium value of a brightness of a driver's head on images detected during the specified number of time frames.

For example, a target brightness may be defined providing optimal conditions for pupil discrimination. By updating the activation time of the illumination sources, a brightness as close as possible to the target brightness may be achieved. For example, the activation time may be updated repeatedly after six time frames. Thus, in case the medium brightness is ascertained to be below the target brightness, the activation time of the illumination sources may be increased while the activation time may be decreased if the medium brightness exceeds the target brightness. A maximum and a minimum activation time can be preset as respective borders for the activation time. The steps to update the activation time may be performed by a computer hardware component like a CPU.

According to another aspect, updating the activation time includes calculating a difference between a preset target brightness value and the medium brightness value and adjusting the activation time based on the calculated difference. Thus, a target brightness value may be predefined and the activation time may be increased or decreased based on the difference between the medium brightness value and the target brightness, wherein the difference may be used as a scale factor for the necessary update of the activation time.

In particular, updating the activation time may further include normalizing the calculated difference according to a normalization rule. The normalized difference may be added to an adjusting parameter. The adjusting parameter may be updated as a minimum of the adjusting parameter and a preset maximum value of the adjusting parameter. The updated activation time may be calculated as a maximum of a preset minimum activation time and a result of a calculation of a minimum of a preset maximum activation time and a present default activation time multiplied by the adjusting parameter. In particular, the default activation time can be half of the maximum activation time.

In principle, several or all of the method steps described herein may be carried out by one or several computer hardware components like a CPU, a microprocessor or a similar processing device. Further, the respective computer hardware component may be a part of a controller for controlling or operating the optical system.

In another aspect, the present disclosure is directed at a computer system, said computer system being configured to carry out several or all steps of the computer implemented method described herein.

The computer system may include a processing device, at least one memory device and at least one non-transitory data storage. The non-transitory data storage and/or the memory device may include a computer program for instructing the computer to perform several or all steps or aspects of the computer implemented method described herein.

In another aspect, the present disclosure is directed at a non-transitory computer readable medium including instructions for carrying out several or all steps or aspects of the computer implemented method described herein. The computer readable medium may be configured as: an optical medium, such as a compact disc (CD) or a digital versatile disk (DVD); a magnetic medium, such as a hard disk drive (HDD); a solid state drive (SSD); a read only memory (ROM), such as a flash memory; or the like. Furthermore, the computer readable medium may be configured as a data storage that is accessible via a data connection, such as an internet connection. The computer readable medium may, for example, be an online data repository or a cloud storage.

The present disclosure is also directed at a computer program for instructing a computer to perform several or all steps or aspects of the computer implemented method described herein.

BRIEF DESCRIPTION OF THE DRAWINGS

Exemplary embodiments and functions of the present disclosure are described herein in conjunction with the following drawings, showing schematically.

DETAILED DESCRIPTION

Figure 1A:
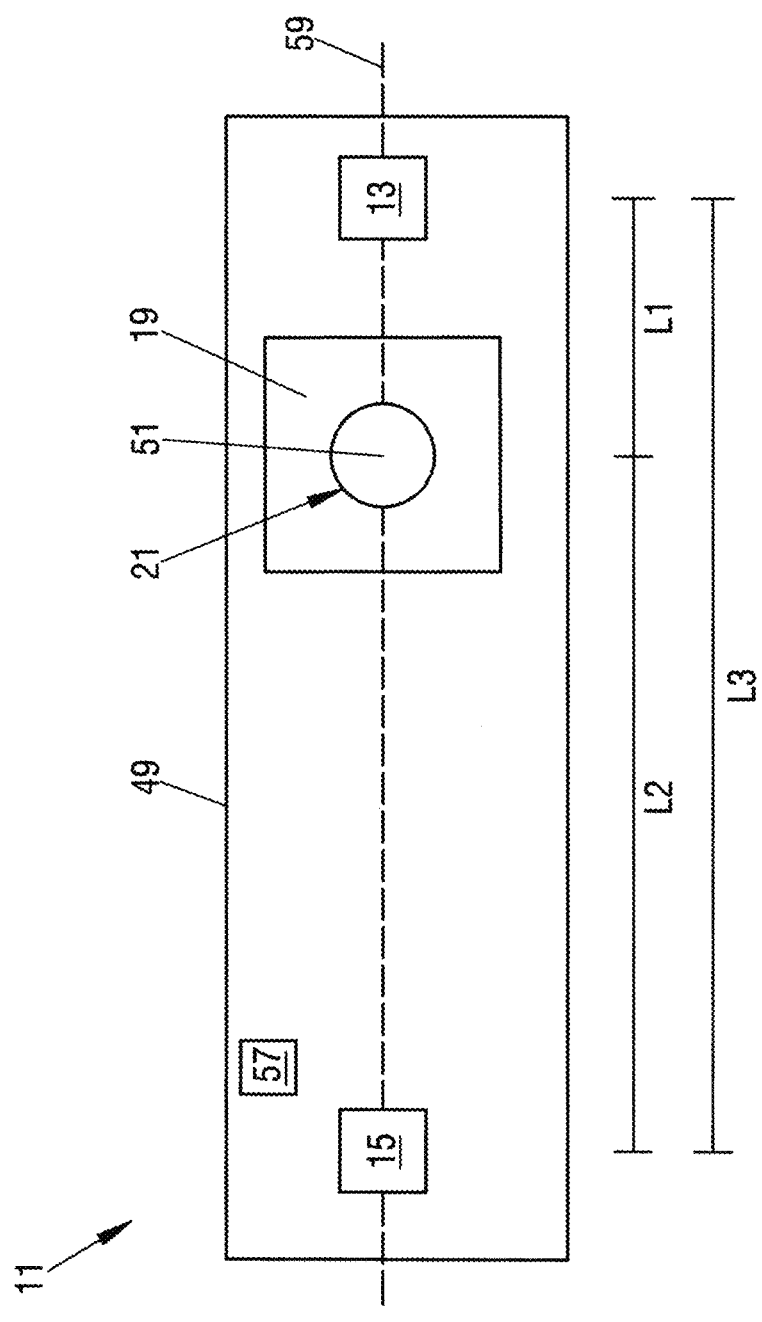
FIGS. 1A and 1B an optical system with a first illumination source and a second illumination source, a lens and an optical sensor for monitoring a vehicle driver's eye gaze, FIG. 2 an illustration of a mixed operation mode and a pure operation mode of the optical system, FIG. 3 a flow diagram illustrating a method for monitoring a vehicle driver's eye gaze with the optical system according to various aspects, FIG. 4 a flow diagram illustrating a method for determining a value of a discriminability parameter used for determining a preferred operation mode of the optical system, FIG. 5 a flow diagram illustrating a method for updating an activation time of the first illumination source and the second illumination source, and FIG. 6 a flow diagram illustrating a method for monitoring a vehicle driver's eye gaze with an optical system.
Figure 1B:
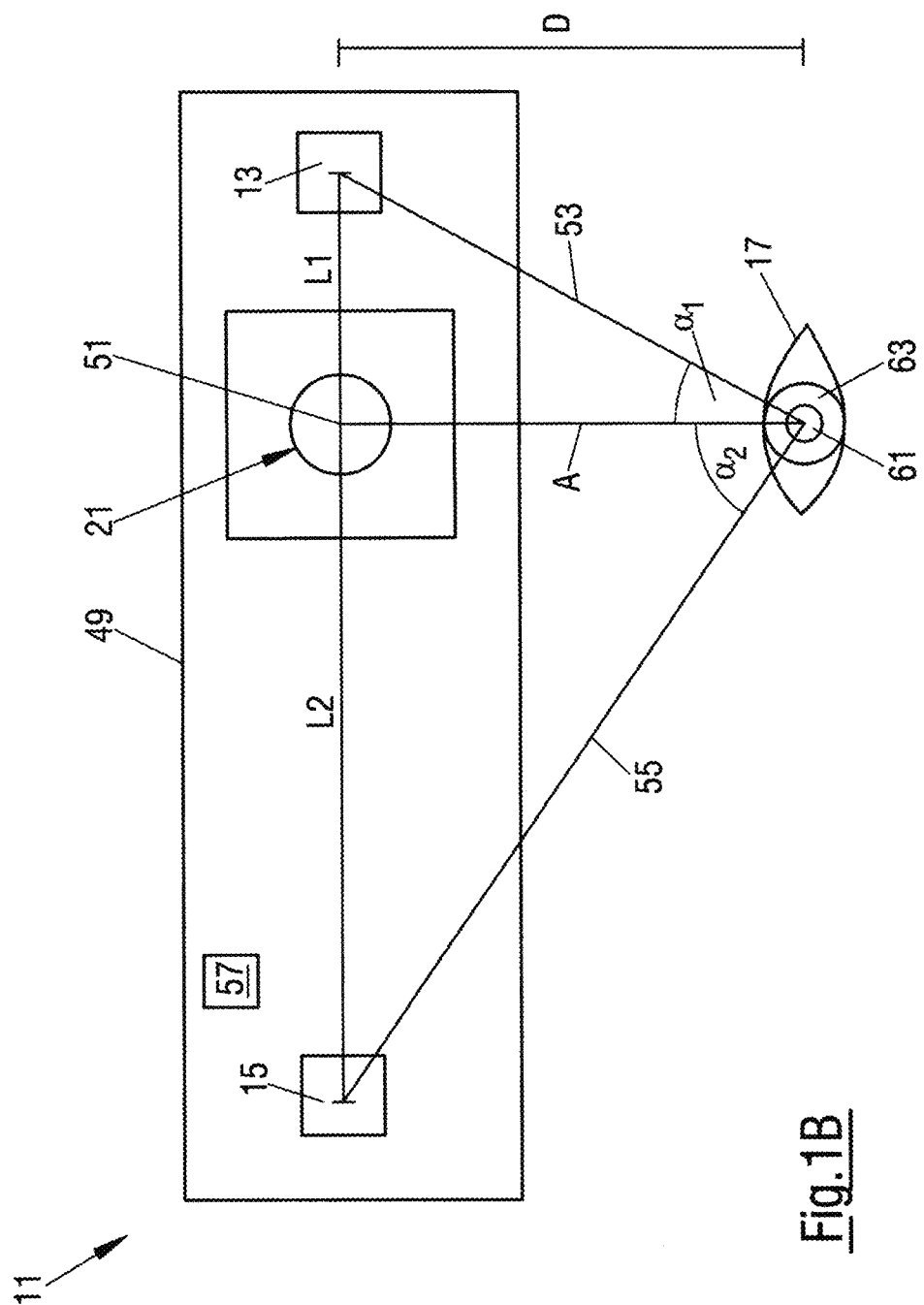

FIG. 1A depicts an optical system 11 that includes a first illumination source 13 and a second illumination source 15 configured to emit light towards a vehicle driver's eye 17 (see also FIG. 1B). Further, a lens 21 is provided for directing light reflected from the vehicle driver's eye 17 to an image sensor 19, on which images of the driver's face or eye 17 may consecutively be taken (see also FIG. 2).

The first illumination source 13, the second illumination source 15 and the lens 21 are arranged in alignment along a line 59 and such that a distance L1 between the first illumination source 13 and an optical axis A or a center 51 of the lens 21 is larger than a distance L2 between the second illumination source 15 and the optical axis A or the center 51 of the lens 21. The illumination sources 13 and 15 as well as the lens 21 and the image sensor 19 are arranged in the common housing 49, such that the optical system 11 is configured as a small packaged driver monitoring camera.

Figure 2:
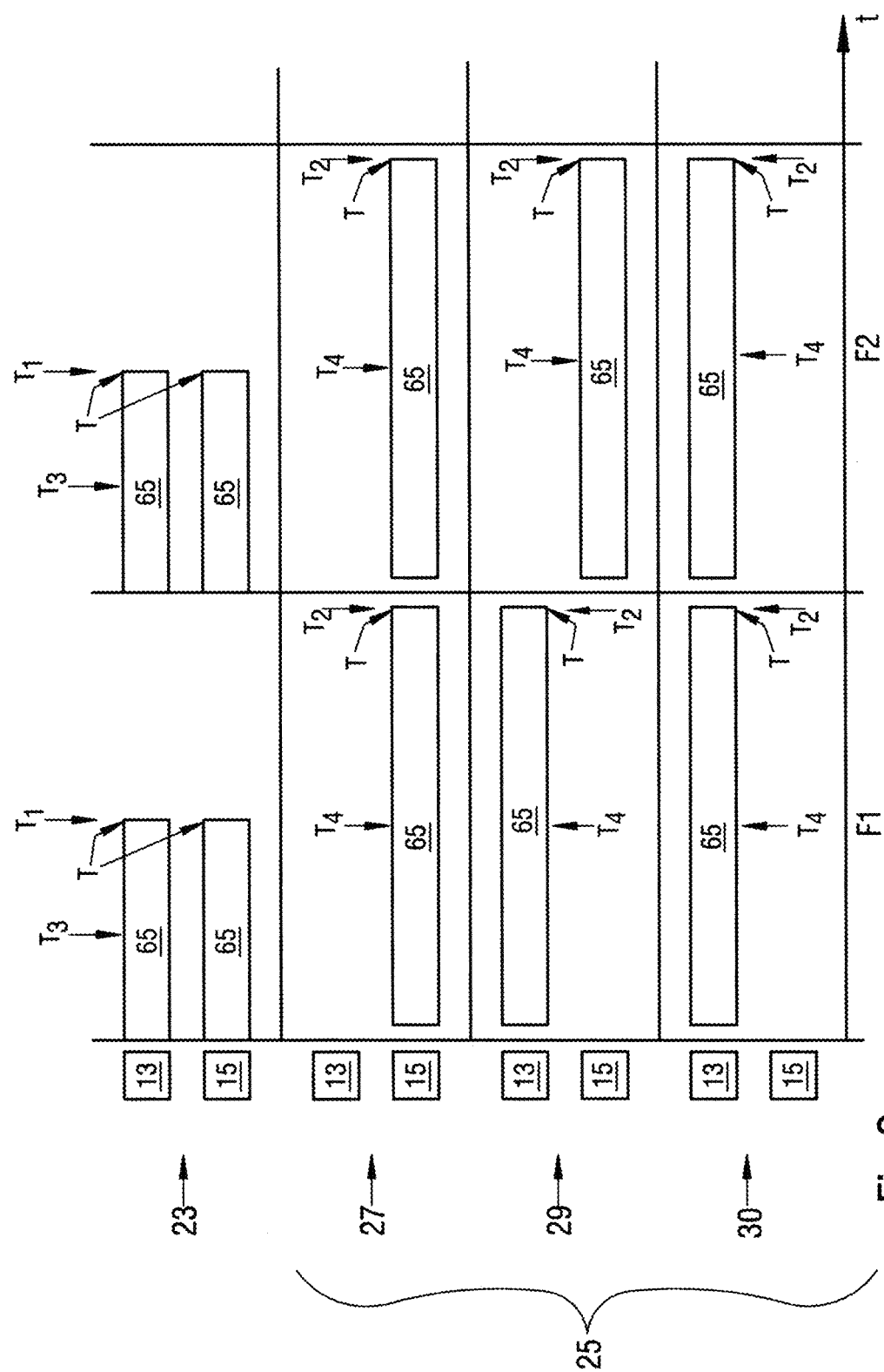

To monitor a vehicle driver's eye gaze with such an optical system 11, images of the driver's eye 17 may be taken consecutively in respective time frames F1 and F2 (see also FIG. 2). Information like the direction into which the driver looks may be inferred by identifying a pupil 61 of the driver in these images, which in particular needs to be distinguished from an iris 63 (see FIG. 1B).

To achieve this, it is possible to illuminate the driver's eye 17 with an on-axis illumination source located close to the lens 21 like the first illumination source 13; such that light reflected by the retina of the eye 17 is directed towards the lens 21 and the pupil 61 may be distinguished as a bright spot in the image. On the other hand, pupil discrimination is possible by illuminating the driver's eye 17 with an off-axis illumination source that is positioned comparably far away from the lens 21 like the second illumination source 15; enabling to discriminate the pupil 61 as a dark spot in an image detected with the image sensor 19.

Common optical systems are configured either as a bright-pupil system with on-axis illumination sources or as dark-pupil systems with off-axis illumination sources. However, pupil discriminability in suchlike systems depends, besides on the design of the system, on external parameters like the ambient light or a distance between the driver's eye and the optical system. For example, for a very small distance D between the driver's eye 17 and the optical system 11, the angle $\alpha_1$ between a connection line 53 between the first illumination source 13 and the driver's eye 17 and the optical axis A may be too large to enable discrimination of the pupil 61 as a bright spot in the image (see also FIG. 1B). On the other hand, an angle z between light emitted from the second illumination source 15 towards the driver's eye 17 along a connection line 55 may be too small to detect the pupil 61 as a bright spot for short distances D between the driver's eye 17 and the optical system 11. Hence, in various situations pupil discrimination may fail in those common systems that are either pure bright-pupil systems or pure dark-pupil systems, potentially resulting in accidents that might have been prevented if reliable eye gaze data could have been provided.

However, with an arrangement of the first illumination source 13 being located close to the lens 21 and the second illumination source 15 being located comparably far away from the lens 21, the optical system may be operated in various operation modes 23, 25, 27, 29 and 30 to flexibly adjust the optical system 11 in dependence on varying environmental conditions or different drivers. Thus, it may be reliably be ensured that the pupil 61 is distinguishable in an image on the image sensor 19 in any situation. Possible operation modes 23, 25, 27, 29 and 30 of the optical system 11 are illustrated in FIG. 2.

Thus, the optical system 11 may be operated in a pure operation mode 25 in which only one of the first illumination source 13 and the second illumination source 15 is activated in a respective time frame F1 or F2, with the activated state of the respective illumination source 13 or 15 being indicated by the numeral 65 in FIG. 2. The time frame F1 is an upcoming time frame F1 and the time frame F2 is a subsequent time frame F2 following the upcoming time frame F1 in time t. However, FIG. 2 only serves as an illustration of possible operation modes 23, 25, 27, 29 and 30 of the optical system 11 without being to scale. Thus, a duration of the time frames F1 and F2 may in particular be longer than an exposure time T2 of the optical system 11. E.g., the exposure time T2 may be of the order of 2 ms (two milliseconds), while the duration of the time frames F1 and F2 may be 16.67 milliseconds (sixteen point six seven milliseconds).

The pure operation mode 25 includes a bright-pupil mode 30 in which only the first illumination source 13 is activated and the optical system 11 is operated as a bright-pupil system. Further, the pure operation mode 25 includes a dark-pupil mode 27 in which only the second illumination source 15 is activated with the optical system 11 being operated as a dark-pupil system. Additionally, a reflection reduction mode 29 is provided in which the first illumination source 13 is activated in an upcoming time frame F1 while the second illumination source 15 is deactivated and in which in a subsequent time frame F2 following the upcoming time frame F1, the second illumination source 15 is activated while the first illumination 13 is deactivated. Hence, the illumination sources 13 and 15 are activated alternately in subsequent time frames F1 and F2 in the reflection reduction mode 29. Further, the optical system 11 may be operated in a mixed operation mode 23, in which the illumination sources 13 and 15 are activated simultaneously.

With this variety of operation modes 23, 25, 27, 29 and 30 provided, a respective preferred operation mode may be determined for the upcoming time frame F1 regarding a certain situation. Accordingly, the optical system 11 may be operated in the preferred operation mode to ensure reliable eye gaze monitoring. For example, in case the driver's eye 17 is located close to the optical system 11, the dark-pupil mode 27 may be the preferred operation mode since the angle $\alpha_2$ is large enough that the pupil 61 occurs as a distinguishable dark spot in the image. Vice versa, the bright-pupil mode 30 may be the preferred operation mode for large distances D between the driver's eye 17 and the optical system 11 ensuring that the angle $\alpha_1$ is small enough for pupil discrimination in the bright-pupil system. While in principle the bright-pupil mode 30 may be provided and preferred for such cases, it has been found that for a huge range of expected driver's eye distances D, reliable pupil discrimination may be achieved by either using the dark-pupil mode 27 or the mixed pupil mode 23. Hence, the pure bright-pupil mode 30 may be omitted in some embodiments of the optical system 11.

Further, to reliably achieve pupil discrimination in as many situations as possible, the optical system 11 is designed such that for an expected range of distances D between the driver's eye 17 and the center 51 of the lens 21, at least the angle $\alpha_1$ is smaller than a predefined bright-pupil angle, the angle $\alpha_2$ is larger than a predefined dark-pupil angle and/or the difference between the angle $\alpha_2$ and the angle $\alpha_1$ is larger than a predefined grey-pupil-shifting angle. In case the angle $\alpha_1$ is smaller than a predefined bright-pupil angle, e.g. 1°, the optical system 11 may be safely operated as a bright-pupil system in the bright-pupil mode 30 or in the mixed operation mode 23 with the pupil 61 being distinguishable as a bright spot in an image. On the other hand, if the angle $\alpha_2$ is larger than a predefined dark-pupil angle, in particular 5°, the pupil 61 reliably occurs as a distinguishable dark spot in an image taken in the dark-pupil mode 27. Further, by ensuring that the difference between $\alpha_2$ and $\alpha_1$ is larger than a predefined grey-pupil-shifting angle, the pupil 61 will be distinguishable as a dark spot in the dark-pupil mode 27 in case it may only be resolved greyish in the bright-pupil mode 30 or the mixed operation mode 23, while the bright-pupil mode 30 and/or the mixed operation mode 23 will reliably enable pupil discrimination in case $\alpha_2$ is too small for pupil discrimination in the dark-pupil mode 27.

In addition, the reflection reduction mode 29 in which the illumination sources 13 and 15 are activated alternately enables to actively reduce reflections distorting the image taken on the image sensor 19, which, e.g., may occur if a vehicle driver is wearing glasses. Hence, the reflection reduction mode 29 may be used to reliably identify the pupil 61 under such aggravated conditions. To reliably achieve reflection reduction, a distance L3 between the first illumination source 13 and the second illumination source L2 may be at least 50 mm.

Figure 6:
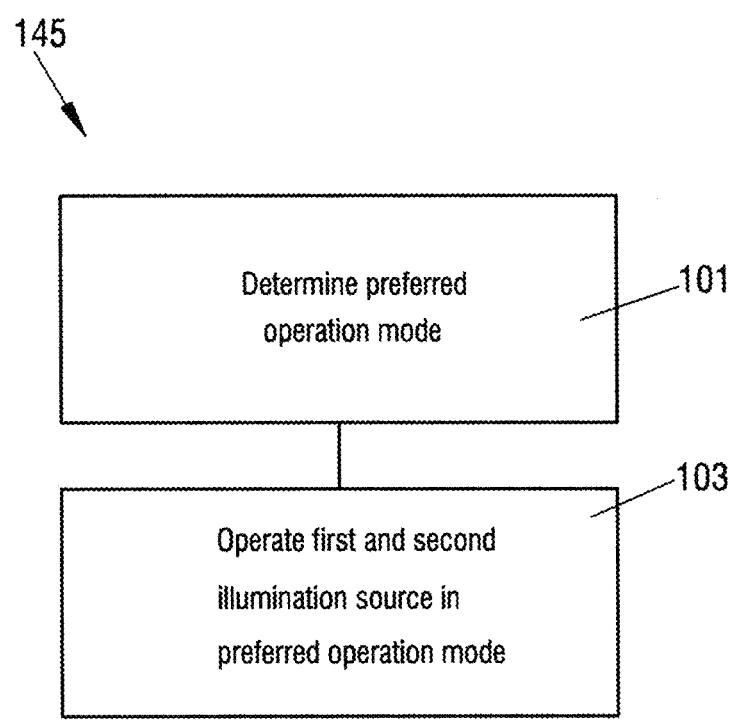

With the variety of operation modes 23, 25, 17, 29 and 30 provided, one of the operation modes 23, 15, 27, 29 and 30 may be preferred under certain circumstances. Hence, for an upcoming time frame F1, a preferred operation mode 23, 25, 27, 29 or 30 can be determined to ensure that the optical system 11 is operated in the preferred operation mode 23, 25, 27, 29 or 30 in this time frame F1. A computer implemented method 145 for monitoring a vehicle driver's eye gaze is illustrated in FIG. 6. In this method, a preferred operation mode of the optical system 11 for the upcoming time frame F1 is determined in a step 101 and the optical system 11 is operated in the preferred operation mode in the upcoming time frame in a step 103. This method 145 may be performed by a controller 57 of the optical system 11. The controller 57 in particular may be configured to activate or deactivate the illumination sources 13 and 15. The controller 57 may include a CPU or a microprocessor for carrying out the steps of the method 145.

Figure 3:
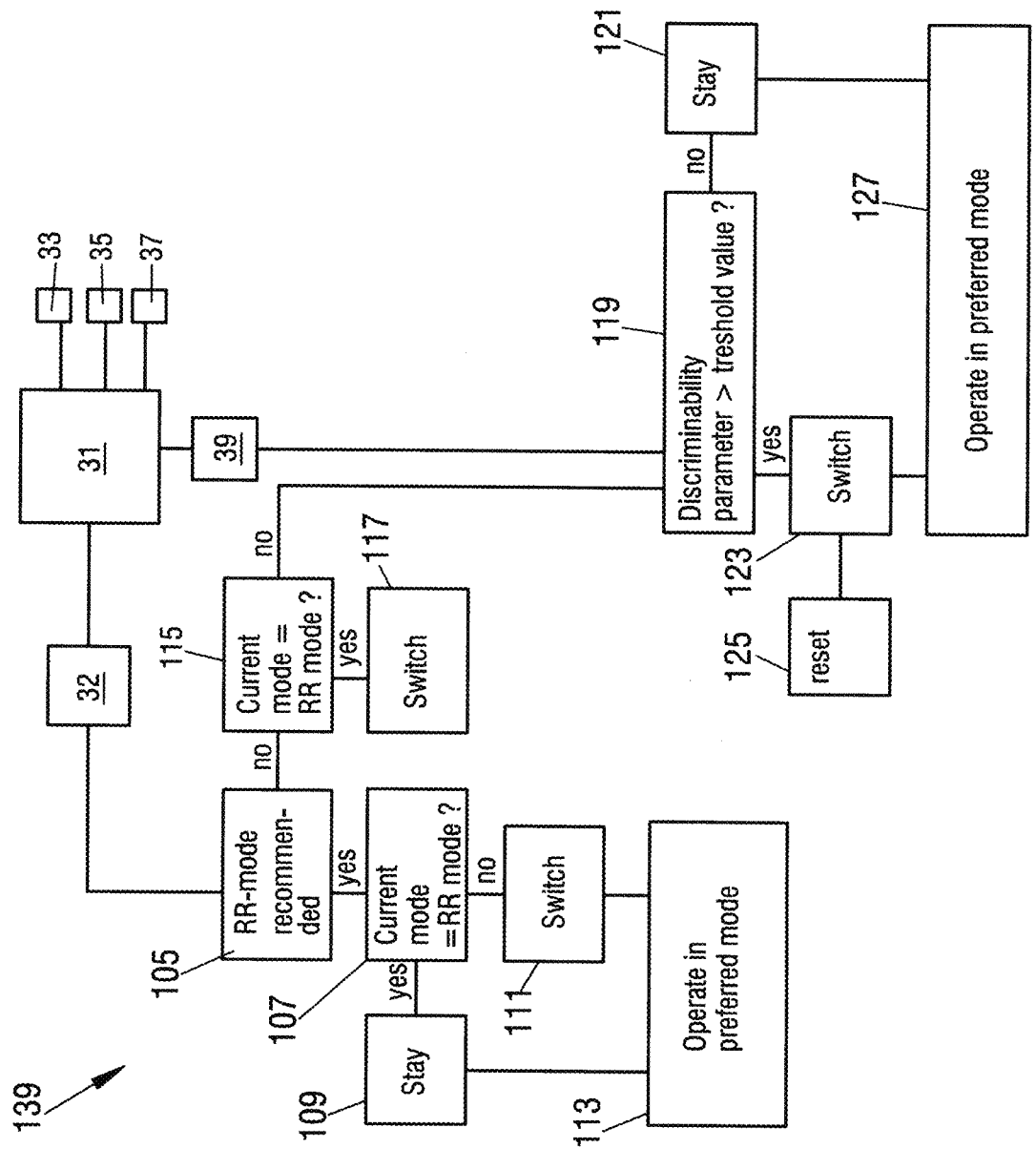

Further, FIG. 3 illustrates a computer implemented method 139 for monitoring a vehicle driver's eye gaze with the optical system 11, which also may be carried out by the controller 57 of the optical system 11 or a CPU or a processing device, which in particular may be a part of the controller 57.

According to the method 139, the preferred operation mode is determined based on a gauge parameter 31. This gauge parameter 31 may include a distance parameter 31 representing the distance D between the driver's eye 17 and the optical system 11, a brightness parameter 35 representing a brightness of ambient light and a pupil size estimation parameter 37 representing an estimated and/or a measured size of the driver's pupil 61. For example, values of these parameters 33, 35 and 37 may be assigned a preferred operation mode of the mixed operation mode 23 and the pure operation mode 25 and the preferred operation mode may be determined based on this assignment after determining a value of the respective parameter 33, 35 and/or 37. For example, if a small distance between the driver's eye 17 and the optical system 11 is detected, the dark-pupil mode 27 may be determined as the preferred operation mode based on the distance parameter 33.

However, in the illustrated method 139, the gauge parameter 31 includes a reflection parameter 32, which represents an estimate and/or a measure of an amount of light emitted towards the driver's eye 17 that is reflected before reaching the eye 17. For example, if the driver is wearing glasses, a high amount of light will be reflected before reaching the driver's eye 17. Therefore, in a first step 105, it is checked based on the reflection parameter 32 whether it is recommended to operate the optical system 11 in the reflection reduction mode 29. In particular, the reflection parameter 32 may be a Boolean parameter representing a binary decision whether to determine the reflection reduction mode 29 as the preferred operation mode.

If the reflection reduction mode 29 is recommended, it is checked in a step 107 whether the optical system 11 is currently operated in the reflection reduction mode 29. In case the reflection reduction mode 29 is the current operation mode, there is no necessity to switch the operation mode and the optical system 11 is instructed to stay in the current operation mode in a step 109. Otherwise, a switch of the optical system 11 to the reflection reduction mode 29 is instructed by the controller 57 in a step 111. Afterwards, the optical system 11 is operated in the reflection reduction mode 29 in the upcoming time frame F1 and, thus, in the preferred operation mode in a step 113.

If, on the other hand, the reflection reduction mode 29 is found not to be recommended in the method step 105, it is checked in a step 115 whether the optical system 11 is currently operated in the reflection reduction mode 29. If this is the case, the optical system 11 is switched to another operation mode 27 or 23 in a step 117. In particular, the mixed operation mode 23 may be determined as the preferred operation mode in the step 117 since the mixed operation mode 23 may be adequate in most situations.

If, however, it is determined in the step 115 that the optical system 11 is currently not operated in the reflection reduction mode 29, a discriminability parameter 39 is acquired and in a step 119 and it is checked whether a value of the discriminability parameter 39 exceeds a preset threshold value, thus indicating to switch from a current operation mode of the mixed operation mode 23 and the pure operation mode 25, in particular the dark-pupil mode 27, to the other operation mode 25 or 23.

Figure 4:
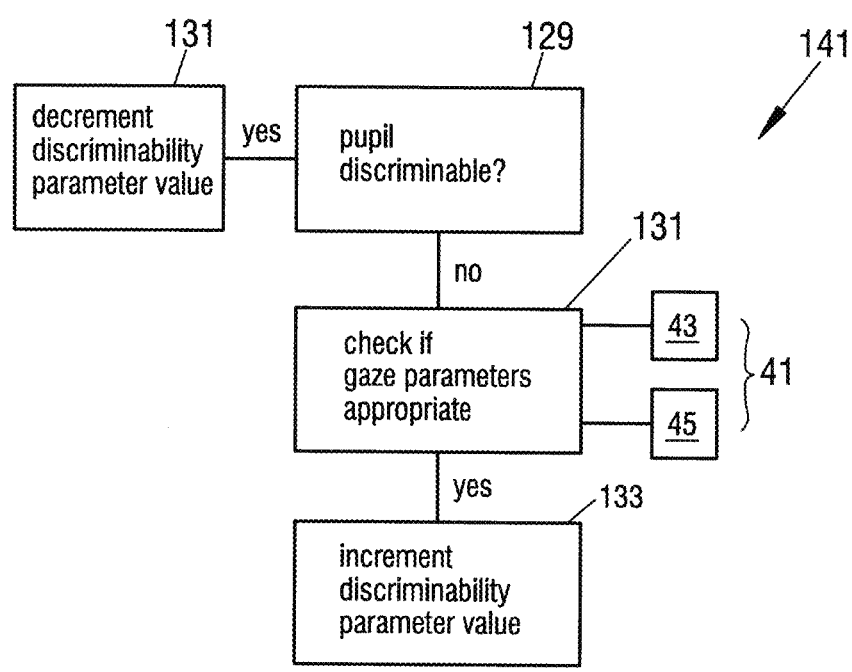
Figure 5:
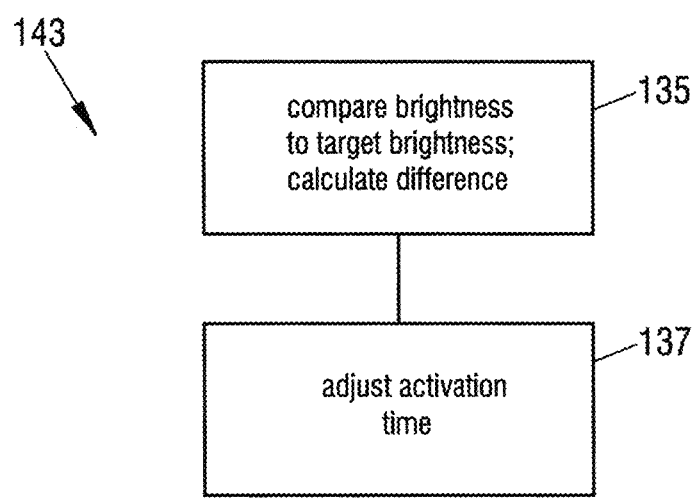

The discriminability parameter 39 may in particular be a counter of images that have been taken consecutively in the current operation mode and in which the pupil 61 could not be discriminated from the iris 63. In particular, the value of the discriminability parameter 39 may be determined according to a computer implemented method 141 as illustrated in FIG. 4. Also the steps of the method 141 may be performed by the controller 57 of the optical system or a computer hardware component like a CPU or a microprocessor. In particular, the controller 57 may include said CPU or microprocessor.

In a first step 129 of this method 141, it is checked whether the pupil 61 could be discriminated in an image that has been taken. In case pupil discrimination worked, the value of the discriminability parameter 39 may be decremented in a step 131. By decrementing the discriminability parameter 39 in case pupil discrimination was successful, randomly occurring images with improper pupil discrimination can be compensated.

If, on the other hand, the pupil 61 could not be discriminated in the image, it is checked in a step 131 if a gaze parameter 41 was in a preset appropriate range. For example, the gaze parameter 41 may include a driver's head yaw 43 and an eye lid opening 45. Only if the gaze parameter 41 was in an appropriate range, i.e. in particular only if the driver was looking comparably straightly towards the optical system 11 with open eyes while the image was taken, the value of the discriminability parameter 39 is incremented by one count. By checking the gaze parameter 41, it is prevented that images taken while the driver's eye 17 was, e.g. closed, are considered as images with improper pupil discrimination due to the optical system being operated in an inadequate operation mode 23 or 25.

The value of the discriminability parameter 39 calculated according to the method 141 may in turn be used and compared with a preset discrimination threshold value in the step 119 of the method 139 illustrated in FIG. 3. This discrimination threshold value may define an acceptable number of images with improper pupil discrimination before the operation mode 23, 25 should be switched from the current operation mode to the other one of the mixed operation mode 23 and the pure operation mode 25. Hence, in case the value of the discriminability parameter 39 does not exceed the threshold value, in a step 121 the optical system 11 is instructed to stay in the current operation mode 23 or 25 as the preferred operation mode. Otherwise, the optical system 11 is switched to the other operation mode 23 or 25 by the controller 57 in a step 123. Further, due to the switch of the operation mode 23, 25, the value of the discriminability parameter 39 is reset to zero counts of images with improper pupil discrimination in a step 125. Afterwards, the optical system 11 is operated in the determined preferred operation mode 23 or 25 in a step 127.

As further follows from FIG. 2, the illumination sources 13 and 15 are activated for a respective activation time T in the mixed operation mode 23 and in the pure operation mode 25. The maximum activation time T1 in the mixed operation mode 23 is half of the maximum activation time T2 in the pure operation mode 25, wherein the maximum activation time T2 in the pure operation mode 25 equals the exposure time T2 of the optical system 11 in the time frames F1 and F2. Since in the mixed operation mode 23 both illumination sources 13 and 15 are activated simultaneously, the smaller maximum activation time T1 ensures that a similar signal to noise ratio may be achieved in both operation modes 23 and 25. This facilitates to reliably identify the pupil 61 using an image evaluation system or algorithm in both operation modes 23 and 25.

While operating the optical system in the preferred operation mode 23 or 25, the actual activation time T in a time frame F1, F2 may be updated within a range between a respective minimum activation time T3 or T4 and a respective maximum activation time T1 and T2 in the mixed operation mode 23 and the pure operation mode 25. As illustrated in FIG. 4, in a method 143 for updating the activation time T, a medium brightness value of the driver's head is compared to a target brightness value in a step 135. For example, the medium brightness value may be calculated based on images taken in six preceding time frames. According to this comparison, in particular according to a difference between the medium brightness value and the target brightness value, the activation time T may be updated in a step 137. The target brightness may be a brightness for which optimal pupil discrimination in the mixed operation mode 23 or the pure operation mode 25 is achievable, such that, starting from a default brightness, the activation time T of the first illumination source 13 and the second illumination source 15 may repeatedly be updated in order to take images with a brightness as close as possible to the target brightness. Also the method 143 may be performed by the controller 57 or a computer hardware component like a CPU or a microprocessor.

Hence, the optical system 11 offers a huge amount of flexibility with various operation modes 23, 25, 27, 29 and 30, in particular the mixed operation mode 23 and the pure operation mode 25. This enables to reliably ensure pupil discrimination in images taken with the optical system 11 for a variety of environmental conditions. Further, the optical system 11 may in particular be configured as a small package driver monitoring camera as a basis or a part of a driving assistance system.

As shown in FIG. 1A, the optical system 11 for monitoring a vehicle driver's eye gaze may at least include: a first illumination source 13 and a second illumination source 15 for emitting light towards the driver's eye 17, a lens 21, and an image sensor 19 for detecting an image, wherein the lens 21 is configured to direct light reflected by the driver's eye 17 to the image sensor 19, and wherein a distance L2 between the second illumination source 13 and an optical axis A of the lens 21 is larger than a distance L1 between the first illumination source 13 and the optical axis A.

The first illumination source, the second illumination source, the lens and the image sensor may be arranged in a common housing.

The lens may be arranged between the first illumination source and the second illumination source.

The first illumination source, the lens and the second illumination source may be arranged in alignment.

A distance between the second illumination source and a center of the lens may be larger than three times a distance between the first illumination source and the center of the lens.

The distance between the first illumination source and the center of the lens may be smaller than or equal to 12 mm and the distance between the second illumination source and the center of the lens may be larger than or equal to 40 mm.

A distance between the first illumination source and the second illumination source may equal at least 50 mm.

The first illumination source, the second illumination source and the lens may be arranged such that for a range of expected driver's eye distances, a driver's eye distance being a distance between the driver's eye and the center of the lens along the optical axis of the lens, at least a first angle between a connection line from the first illumination source to the expected location of the driver's eye and the optical axis being equal to or smaller than a predefined bright-pupil angle, in particular wherein the bright-pupil angle equals 1° (1 degree), and/or a second angle between a connection line from the second illumination source to the expected location of the driver's eye and the optical axis being larger than a predefined dark-pupil angle, in particular wherein the dark-pupil angle equals 5° (5 degrees), and/or a difference angle between the second angle and the first angle being larger than a predefined grey-pupil-shifting angle is fulfilled.

The optical system may include a controller, the controller being configured to carry out methods disclosed herein.

As shown in FIG. 6, a computer implemented method 145 for monitoring a vehicle driver's eye gaze with an optical system 11, in particular an optical system 11 as disclosed herein, is illustrated. The optical system 11, as shown in FIG. 1A, includes at least a first illumination source 13 and a second illumination source 15 for emitting light towards the driver's eye 17 and a lens 21 for directing light reflected by the driver's eye 17 to an image sensor 19, wherein a distance L1 between the second illumination source 15 and an optical axis A of the lens 21 is larger than a distance L1 between the first illumination source 13 and the optical axis A, and wherein in consecutive time frames F1, F2 at least one image of the driver's eye 17 is detected per time frame F1, F2. At 101 a preferred operation mode 23, 25 of the optical system 11 for an upcoming time frame F1 is determined, the preferred operation 23, 25 mode being one of at least a mixed operation mode 23 and a pure operation mode 25. At 103, the optical system 11 is operated according to the preferred operation mode 23, 25 in the upcoming time frame F1, F2. In the mixed operation mode 23, the first illumination source 13 and the second illumination source 15 are activated simultaneously in the upcoming time frame F1, and in the pure operation mode 25, one of the first illumination source 13 and the second illumination source 15 is at least temporarily activated while the other one of the first illumination source 13 and the second illumination source 15 is deactivated in the upcoming time frame F1, as shown in FIG. 2.

The preferred operation mode may be determined based on at least one gauge parameter, the gauge parameter being at least one of: a distance parameter representing an estimated and/or measured distance between the driver's eye and the optical system, in particular a distance between the driver's eye and a center of the lens along the optical axis; a brightness parameter representing a brightness of ambient light; a reflection parameter representing an estimate and/or a measure of an amount of light being reflected before reaching the driver's eye; a pupil size estimation parameter representing an estimated and/or measured size of the driver's pupil; and a discriminability parameter representing a discriminability of the driver's pupil in at least one image detected with the image sensor during at least one preceding time frame operated in a current operation mode, the current operation mode being one of the mixed operation mode and the pure operation mode.

The preferred operation mode may be one of the current operation mode of the mixed operation mode and the pure operation mode and the other of the mixed operation mode and the pure operation mode and determining the preferred operation mode may include: determining, based on the gauge parameter, whether it is necessary to switch from the current operation mode to the other operation mode in order to obtain an image in which the driver's pupil is distinguishable in the upcoming time frame; and determining the other operation mode as the preferred operation mode if the gauge parameter indicates a necessity to switch to the other operation mode.

The gauge parameter may include at least the discriminability parameter, a value of the discriminability parameter being a counter of images with improper pupil discrimination detected in preceding time frames consecutively operated in the current operation mode, and the other operation mode may be determined as the preferred operation mode if the discriminability parameter exceeds a preset discrimination threshold value defining a maximum number of images with improper pupil discrimination.

The value of the discriminability parameter may be incremented by one count if an image with improper pupil identification is detected in a time frame and if at least one gaze parameter is detected to be in a predefined appropriate range, the at least one gaze parameter being at least one of a driver's head yaw, a driver's eye lid opening and/or a distance between a driver's head and the optical system.

The value of the discriminability parameter may be incremented by one count if an image with improper pupil identification is detected in a time frame and if at least the driver's head yaw and the driver's eye lid opening are in a predefined appropriate range.

The value of the discriminability parameter may be decremented by one count if an image with proper pupil discrimination is detected in a time frame.

The pure operation mode may include a dark-pupil mode in which the second illumination source is at least temporarily activated in the upcoming time frame and the first illumination source is deactivated in the upcoming time frame, wherein the dark-pupil mode may be determined as the preferred operation mode if the mixed operation mode is the current operation mode and if the value of the discrimination parameter exceeds the discrimination threshold value.

The pure operation mode may include a reflection reduction mode in which one of the first illumination source and the second illumination source is at least temporarily activated while the other one of the first illumination source and the second illumination source is deactivated in the upcoming time frame and in which the other one of the first illumination source and the second illumination source is at least temporarily activated while the one of the first illumination source and the second illumination source is deactivated in a subsequent time frame following the upcoming time frame.

The preferred operation mode may be determined based on at least a reflection parameter representing an estimate and/or a measure of an amount of light being reflected before reaching the driver's eye and the reflection reduction mode may be determined as the preferred operation mode if the reflection parameter indicates a high amount of light emitted towards the driver's eye being reflected before reaching the driver's eye.

The first illumination source and/or the second illumination source may be activated for a respective activation time in the mixed operation mode and in the pure operation mode, wherein a maximum activation time in the mixed operation mode may be half of an exposure time of the optical system in the time frames.

The maximum activation time in the mixed operation mode may be half of a maximum activation time in the pure operation mode and a minimum activation time in the mixed operation mode may be half of a minimum activation time in the pure operation mode.

The activation time may be updated after a specified number of time frames according to a medium brightness value of images detected in the specified number of time frames, in particular wherein the medium brightness value represents a medium value of a brightness of a driver's head on images detected during the specified number of time frames.

Updating the activation time may include: calculating a difference between a preset target brightness value and the medium brightness value; adjusting the activation time based on the calculated difference.

A computer system may be configured to carry out the computer implemented methods disclosed herein.

A non-transitory computer readable medium may include instructions for carrying out the computer implemented methods disclosed herein.

What is claimed is:

1. A system comprising:
   a first illumination source configured to emit light toward an eye of a driver of a vehicle;
   a second illumination source configured to emit light toward the eye;
   a lens configured to direct light that has been reflected by the eye from at least one of the first illumination source or the second illumination source to an image sensor, a distance between an optical axis of the lens and the second illumination source being larger than a distance between the optical axis and the first illumination source;
   the image sensor configured to capture image data of the eye via the light from the lens; and
   a controller configured to:
     receive the image data from the image sensor;
     determine a preferred operation mode of the system for an upcoming time frame, the preferred operation mode being one of at least a mixed operation mode or a pure operation mode,
       the mixed operation mode comprising activating the first illumination source and the second illumination source simultaneously for a mixed operation mode activation time and, following the activation of the first illumination source and the second illumination source, deactivating the first illumination source and the second illumination source simultaneously in the upcoming time frame, and
       the pure operation mode comprising at least temporarily activating one of the first illumination source and the second illumination source for a pure operation mode activation time while the other one of the first illumination source and the second illumination source is deactivated in the upcoming time frame, the pure operation mode activation time being greater than the mixed operation mode activation time; and
     operate the system according to the preferred operation mode in the upcoming time frame.

2. The system of claim 1, wherein:
   the system further comprises a common housing;

the first illumination source, the second illumination source, the lens, and the image sensor are arranged in the common housing; and
the lens is arranged between the first illumination source and the second illumination source.

3. The system of claim 2, wherein the first illumination source, the lens, and the second illumination source are further arranged along a line perpendicular to the optical axis.

4. The system of claim 2, wherein a distance between the second illumination source and a center of the lens is greater than three times a distance between the first illumination source and the center of the lens.

5. The system of claim 4, wherein:
the distance between the first illumination source and the center of the lens is less than or equal to 12 mm, and
the distance between the second illumination source and the center of the lens is greater than or equal to 40 mm.

6. The system of claim 5, wherein a distance between the first illumination source and the second illumination source is at least 50 mm.

7. The system of claim 1, wherein the first illumination source, the second illumination source, and the lens are arranged such that, for a range of expected driver's eye distances between the eye and a center of the lens along the optical axis,
a first angle between a line extending from the first illumination source to an expected location of the eye and the optical axis is less than or equal to a predefined bright-pupil angle.

8. The system of claim 1, wherein the first illumination source, the second illumination source, and the lens are arranged such that, for a range of expected driver's eye distances between the eye and a center of the lens along the optical axis,
a second angle between a line extending from the second illumination source to an expected location of the eye and the optical axis is greater than a predefined dark-pupil angle.

9. The system of claim 1, wherein the first illumination source, the second illumination source, and the lens are arranged such that, for a range of expected driver's eye distances between the eye and a center of the lens along the optical axis,
a difference angle between a second angle that is between a line extending from the second illumination source to an expected location of the eye and the optical axis and a first angle that is between a line extending from the first illumination source to the expected location of the eye and the optical axis is greater than a predefined gray-pupil-shifting angle.

10. A method comprising:
determining, by a controller, a preferred operation mode of an optical system for an upcoming time frame,
the optical system comprising at least a first illumination source and a second illumination source for emitting light toward a driver's eye and a lens for directing light reflected by the driver's eye to an image sensor and a distance between the second illumination source and an optical axis of the lens being larger than a distance between the first illumination source and the optical axis,
the preferred operation mode being one of at least a mixed operation mode or a pure operation mode,
the mixed operation mode comprising activating the first illumination source and the second illumination source simultaneously for a mixed operation mode activation time and, following the activation of the first illumination source and the second illumination source, deactivating the first illumination source and the second illumination source simultaneously in the upcoming time frame, and
the pure operation mode comprising at least temporarily activating one of the first illumination source and the second illumination source for a pure operation mode activation time while the other one of the first illumination source and the second illumination source is deactivated in the upcoming time frame, the pure operation mode activation time being greater than the mixed operation mode activation time; and
operating the optical system according to the preferred operation mode in the upcoming time frame.

11. The method of claim 10, wherein the determining the preferred operation mode is based on at least one gauge parameter, the gauge parameter being at least one of:
a distance parameter representing an estimated or measured distance between the driver's eye and a center of the lens along the optical axis;
a brightness parameter representing a brightness of ambient light;
a reflection parameter representing an estimate or a measure of an amount of light being reflected before reaching the driver's eye;
a pupil size estimation parameter representing an estimated or measured size of a pupil of the driver's eye; or
a discriminability parameter representing a discriminability of the pupil in at least one image detected with the image sensor during at least one preceding time frame operated in a current operation mode, the current operation mode being one of the mixed operation mode or the pure operation mode.

12. The method of claim 11, wherein the determining the preferred operation mode comprises:
determining, based on the gauge parameter, whether to switch from the current operation mode to another operation mode to obtain an image in which the pupil is distinguishable in the upcoming time frame.

13. The method of claim 11, wherein:
the gauge parameter comprises at least the discriminability parameter;
a value of the discriminability parameter is a counter of images with improper pupil discrimination detected in preceding time frames consecutively operated in the current operation mode; and
the determining whether to switch from the current operation mode to the other operation mode comprises determining to switch from the current operation mode to the other operation mode when the discriminability parameter exceeds a preset discrimination threshold value defining a maximum number of images with improper pupil discriminability.

14. The method of claim 13, wherein:
the value of the discriminability parameter is incremented by one count when an image with improper pupil identification is detected in the time frame and when at least one gaze parameter is detected to be in a predefined appropriate range, the at least one gaze parameter being at least one of a driver's head yaw, a driver's eye lid opening, or a distance between a driver's head and the optical system; or the value of the discriminability parameter is decremented by one count when an image with proper pupil discrimination is detected in the time frame.

15. The method of claim 13, wherein:
the current operation mode comprises the mixed operation mode;
the value of the discriminability parameter exceeds the discrimination threshold value;
the pure operation mode further comprises a dark-pupil mode in which the second illumination source is at least temporarily activated in the upcoming time frame and the first illumination source is deactivated in the upcoming time frame; and
the determining whether to switch from the current operation mode to the other operation mode comprises determining to switch from the mixed operation mode to the dark-pupil mode.

16. The method of claim 10, wherein:
the pure operation mode further comprises a reflection reduction mode in which one of the first illumination source or the second illumination source is at least temporarily activated while another of the first illumination source or the second illumination source is deactivated in the upcoming time frame; and
the other of the first illumination source or the second illumination source is at least temporarily activated while the one of the first illumination source and the second illumination source is deactivated in a subsequent time frame following the upcoming time frame.

17. The method of claim 16, wherein:
the determining the preferred operation mode based on at least a reflection parameter representing a gauge or a measure of an amount of light being reflected before reaching the driver's eye; and
the preferred operation mode comprises the reflection reduction mode when the reflection parameter indicates a high amount of light emitted toward the driver's eye being reflected before reaching the driver's eye.

18. The method of claim 10, wherein a maximum value of the mixed operation mode activation time is half a maximum value of the pure operation mode activation time.

19. The method of claim 18, wherein:
a medium brightness value is calculated for a plurality of previous time frames that represents a medium value of respective brightness's of a driver's head on images detected during the previous time frames; and
the mixed operation mode activation time and the pure operation mode activation time are determined for the upcoming time frame based on a difference between a preset target brightness value and the medium brightness value.

20. A non-transitory computer readable medium comprising program instructions for causing one or more computing devices of a system to:
determine a preferred operation mode of an optical system for an upcoming time frame,
the optical system comprising at least a first illumination source and a second illumination source for emitting light toward a driver's eye and a lens for directing light reflected by the driver's eye to an image sensor and a distance between the second illumination source and an optical axis of the lens being larger than a distance between the first illumination source and the optical axis,
the preferred operation mode being one of at least a mixed operation mode or a pure operation mode,
the mixed operation mode comprising activating the first illumination source and the second illumination source simultaneously for a mixed operation mode activation time and, following the activation of the first illumination source and the second illumination source, deactivating the first illumination source and the second illumination source simultaneously in the upcoming time frame, and
the pure operation mode comprising at least temporarily activating one of the first illumination source and the second illumination source for a pure operation mode activation time while the other one of the first illumination source and the second illumination source is deactivated in the upcoming time frame, the pure operation mode activation time being greater than the mixed operation mode activation time; and
operate the optical system according to the preferred operation mode in the upcoming time frame.

* * * * *